United States Patent [19]

Sakurai et al.

[11] Patent Number: 4,628,047
[45] Date of Patent: Dec. 9, 1986

[54] AGENT FOR ENHANCING ANTITUMOR ACTIVITY OF ANTITUMOR AGENT

[75] Inventors: Yoshio Sakurai, Mitaka; Takashi Tsuruo, Tokyo, both of Japan

[73] Assignees: Japanese Foundation for Cancer Research, Tokyo; Tanabe Seiyaku Co., Ltd., Osaka, both of Japan

[21] Appl. No.: 498,639

[22] Filed: May 27, 1983

[30] Foreign Application Priority Data

May 28, 1982 [JP] Japan .................................. 57-91850

[51] Int. Cl.$^4$ ..................... A61K 31/70; A61K 31/55; A61K 31/44
[52] U.S. Cl. ..................................... 514/34; 514/211; 514/281; 424/10
[58] Field of Search ......................... 424/244, 262, 10; 514/281, 34, 211

[56] References Cited

PUBLICATIONS

Chemical Abstracts 99:16207c (1983).
Chemical Abstracts 99:205713a (1983).
The Merck Index, 9th Edition, Monograph 3187.
The Extra Pharmacopoeia, Martindale, 27th Edition, p. 1750.

Primary Examiner—Jerome D. Goldberg
Attorney, Agent, or Firm—Birch, Stewart, Kolasch & Birch

[57] ABSTRACT

An agent for enhancing antitumor activity of antitumor agents comprising as the active ingredient diltiazem or a pharmaceutically acceptable acid addition salt thereof, an antitumor composition comprising the diltiazem or an acid addition salt thereof and a conventional antitumor agent, and further a method for treating tumors by administering diltiazem or an acid addition salt thereof together with a conventional antitumor agent in oral or parenteral route to patients suffering from various tumors. Said active diltiazem or a salt thereof is effective for enhancing the antitumor activity of antitumor agents because it can enhance sensitivity of tumor cells to antitumor agents regardless the tumor cells have resistance to the antitumor agents or not.

3 Claims, 1 Drawing Figure

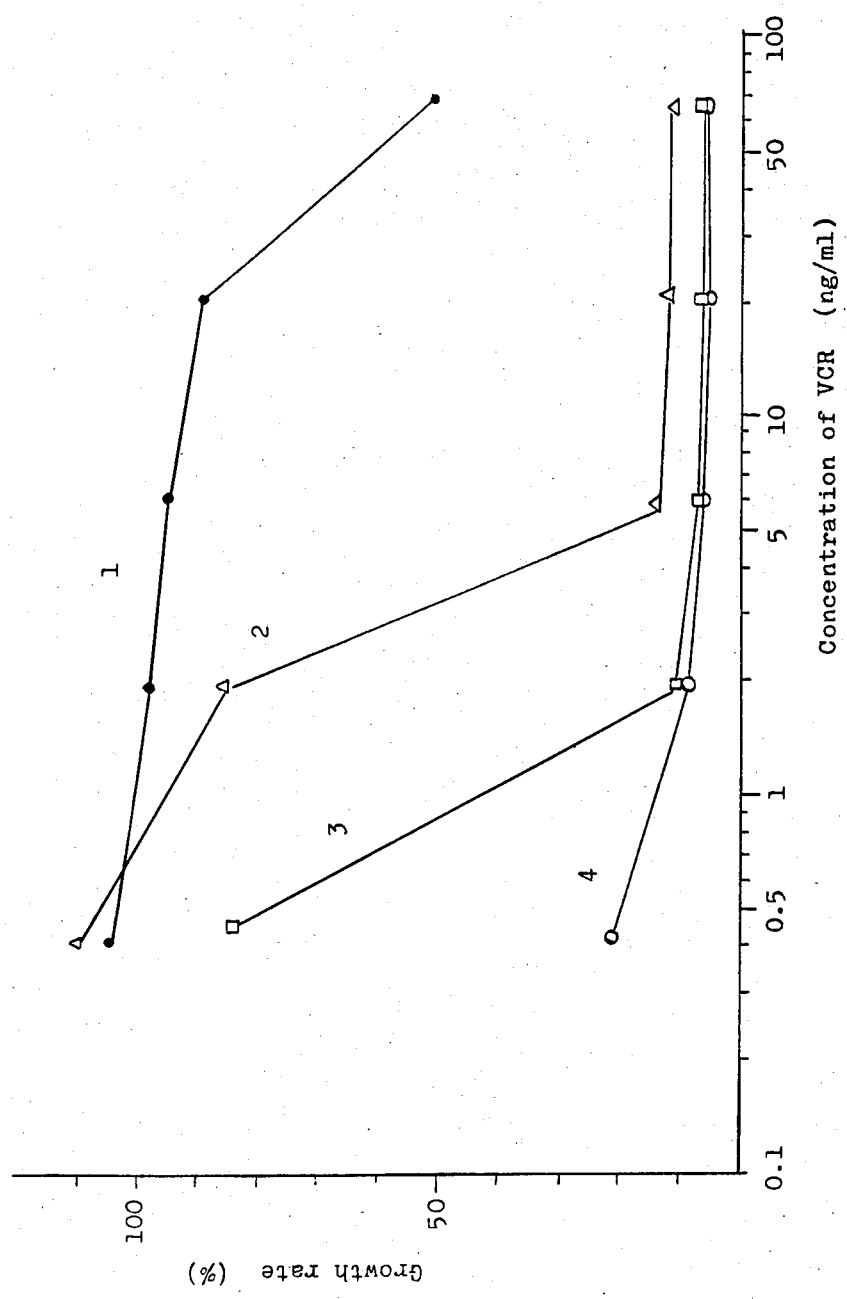

AGENT FOR ENHANCING ANTITUMOR ACTIVITY OF ANTITUMOR AGENT

The present invention relates to the use of diltiazem as an agent for enhancing the therapeutic effect of the antitumor agents vincristine and doxorubicine in a composition which comprises as the active ingredient diltiazem or a pharmaceutically acceptable acid addition salt thereof for the treatment of chronic lymphatic leukemia, chronic myelogenous leukemia and Hodgkin's disease.

It is known that diltiazem (chemical name: d-3-acetoxy-cis-2,3-dihydro-5-[2-(dimethylamino)ethyl]-2-(p-methoxyphenyl)-1,5-benzothiazepin-4(5H)-one) has potent coronary vasodilating activity and is useful as a coronary circulation-stimulant, but it has never been known that this compound shows an effect for enhancing the antitumor activity of an antitumor agent.

Generally, it is difficult to cure the tumors completely when chemotherapeutic agents for treating various tumors, such as leukemia, lymphoma and solid tumor, are used alone, because of the different sensitivity of tumor cells to each antitumor agent, i.e. heterogenity. Besides, when an antitumor agent is used continuously, the tumor cells gain resistance (acquired resistance) to the antitumor agent. For instance, it is known that vinca alkaloids such as vincristine and vinblastine isolated from Vinca Rosea, Apocynaceae, or doxorubicin isolated from cultures of a mutant Streptomyces peucetius show potent antitumor activity against lymphatic leukemia, myelogenous leukemia and Hodgkin's disease, but the tumor cells gain resistance to these agents when they are used continuously for a long period of time. One of the other serious problems in therapeutic treatment of tumors or leukemia is that cross-resistance induced between antitumor agents of a similar structure makes it difficult for the antitumor agent to attain the expected therapeutic effect.

As a result of the present inventors' intensive study, it has unexpectedly been found that when the known coronary vosodilator, diltiazem, is used together with an antitumor agent, it can remarkably enhance the therapeutic effect of the antitumor agent.

An object of the present invention is to provide an agent for enhancing the therapeutic effect of an antitumor agent comprising as the active ingredient diltiazem or a pharmaceutically acceptable acid addition salt thereof. Another object of the invention is to provide an antitumor composition comprising as the active ingredient diltiazem or a pharmaceutically acceptable acid addition salt thereof and an antitumor agent. A further object of the invention is to provide a method for treating tumors by administering diltiazem or a pharmaceutically acceptable acid addition salt thereof together with a conventional antitumor agent to a warm-blooded animal suffering from various tumors. These and other objects and advantages of the present invention will be apparent to persons skilled in the art from the following description.

The agent of the present invention for enhancing the antitumor activity of an antitumor agent comprises as the active ingredient diltiazem or a pharmaceutically acceptable acid addition salt thereof. The agent of the present invention can enhance sensitivity of not only tumor cells having no resistance to antitumor agents, so-called virgin cells, but also tumor cells having resistance to the antitumor agents. Accordingly, when this agent is used together with an antitumor agent, the growth of tumor cells can almost completely be inhibited regardless of whether the tumor cells have resistance to the antitumor agent or not. That is, when an antitumor agent is used alone, tumor cells having resistance to the agent usually remain alive and again grow resulting in a relapse of tumor cell growth. However, when diltiazem is used together with the antitumor agent, the tumor cells having resistance to the antitumor agent show highly increased sensitivity to the antitumor agent and do not show resistance to the antitumor agent, which results in an effective inhibition of tumor cell growth and hence in complete remedy of tumor and inhibition of relapse.

Moreover, antitumor agents are usually used in a maximum dose in order to expect the highest therapeutic effect, but the dose of the antitumor agent can be reduced by using it together with the agent of the present invention because the agent of the present invention can enhance the sensitivity of tumor cells to the antitumor agent. Thus, when the antitumor agent is used together with the agent of the present invention, it can exhibit the desired antitumor activity in a lower dose with less toxicity. For instance, in an experiment using P388 leukemia cells having resistance to vincristine, when vincristine is used alone, it must be administered in a dose of 60 ng/ml for showing 50% inhibition of the tumor cells, but on the other hand, when vincristine is used together with diltiazem (hydrochloride) at a concentration of 35 $\mu$M or 100 $\mu$M, it can show 50% inhibition of the resistant cells in a concentration of vincristine of 1 ng/ml or less. In an experiment using P388 leukemia cells having resistance to doxorubicin, when doxorubicin is used alone, it must be administered in a dose of 592 ng/ml for showing 50% inhibition of the tumor cells, but on the other hand, when doxorubicin is used together with diltiazem at 100 $\mu$M, it can show 50% inhibition of the cells in a concentration of about 30 ng/ml.

The active compound, diltiazem, may be used in the form of a free base or a pharmaceutically acceptable acid addition salt thereof. The pharmaceutically acceptable acid addition salt includes organic acid salts such as acetate, oxalate, malonate, tartrate, citrate, lactate, or aspartate, and inorganic acid salts such as hydrochloride, hydrobromide, sulfate, nitrate, or perchlorate.

Diltiazem or an acid addition salt thereof may be used together with various antitumor agents, for example, antitumor antibiotics such as daunorubicin, doxorubicin and antitumor plant alkaloids such as vincristine are particularly preferably used together with the agent of the present invention.

The dose of diltiazem or an acid addition salt thereof may vary according to the administration routes, age of patients, severity of diseases and also kinds of the antitumor agents used together, but is usually in the range of 1 mg/kg to 20 mg/kg, preferably 5 mg/kg to 15 mg/kg, per day.

The dose of the antitumor agent to be used together with diltiazem or an acid addition salt thereof is not critical, but is in the range usually used, that is, in the range of 10 $\mu$g to 30 mg, preferably 0.005 to 20 mg, more preferably 0.01 to 10 mg, particularly 0.01 to 3 mg. For example, doxorubicin is administered intravenously in a dose of about 0.2 to 3 mg/kg; and vincristine is administered in a dose of 0.01 to 0.2 mg/kg.

Thus, diltiazem or a pharmaceutically acceptable acid addition salt is useful for the method of treating or preventing various malignant tumors by administering it together with an conventional antitumor agent to a warm-blooded animal, including human, suffering from said malignant tumors.

Diltiazem or an acid addition salt thereof and the antitumor agent may be administered in any manner and in any form of pharmaceutical preparations. For instance, both agents can be administered in oral and parenteral routes. They may be administered in the form of a combined preparation or separately. In the latter form, i.e. when administered separately, they may be used in the same dosage form or in the different dosage form. For instance, in some kinds of antitumor agents, both diltiazem, or an acid addition salt thereof, and the antitumor agent may be administered orally, or the antitumor agent may be administered parenterally and diltiazem or an acid addition salt thereof may be administered orally. Antitumor agents are usually administered intermittently or continuously taking into consideration their effect and toxicity, and in any case, the agent of the present invention can exhibit the enhancement of the antitumor activity of the antitumor agent.

Diltiazem or an acid addition salt thereof and the antitumor agents can be used in the form of conventional preparations in admixture with conventional pharmaceutically acceptable carrier or diluent. The pharmaceutically acceptable carrier or diluent for the preparations of diltiazem or an acid addition salt and for the oral preparations of antitumor agents include, for example, binding agents (e.g. syrup, gum arabic, gelatine, sorbitol, tragacanth, polyvinyl pyrrolidone, etc.), excipients (e.g. lactose, sucrose, cornstarch, potassium phosphate, sorbitol, glycine, etc.), lubricants (e.g. magnesium stearate, talc, polyethylene glycol, silica, etc.), disintegrators (e.g. potato starch, etc.), wetting agents (e.g. sodium laurylsulfate, etc.). The preparations include conventional pharmaceutical preparations such as tablets, pills, powders, capsules, and granules.

For parenteral administration, the compositions may be used in the form of injection and drip infusion in admixture with distilled water for injection, physiological saline solution or aqueous glucose solution, or in the form of suspension, dispersion or emulsion in admixture with glycerine, propylene glycol, simple syrup, ethanol, fatty oils, ethylene glycol, sorbitol, or the like.

In the pharmaceutical preparation of diltiazem or a pharmaceutically acceptable acid addition salt thereof to be used for enhancement of the antitumor activity of an antitumor agent, the diltiazem or an acid addition salt thereof is incorporated in an amount of 10 to 120 mg, preferably 20 to 100 mg, in a dosage unit. In the preparation of diltiazem or a pharmaceutically acceptable acid addition salt thereof and an antitumor agent, i.e. an antitumor composition, the diltiazem or an acid addition salt thereof is incorporated in an amount of 10 to 120 mg, preferably 20 to 100 mg, and the antitumor agent is incorporated in an amount of 3 μg to 30 mg, preferably 0.005 to 15 mg, more preferably 0.003 to 3 mg, in a dosage unit.

The agent of the present invention for enhancing the therapeutic effect of an antitumor agent can be used for treating various malignant tumors when used together with various antitumor agents. The tumors applicable, which depend on the used antitumor agents, are, for example Hodgkin's disease, reticulosarcoma, acute leukemia, chronic lymphatic leukemia, chronic myelogenous leukemia, multiple myeloma, deciduocellular sarcoma, Wilms tumor, neuroblatoma, rhabdomyosarcoma, carcinoma planoepitheliale, lung cancer, mammary cancer, ovary cancer, ueterine cancer, stomach cancer, colon cancer, hepatic cancer, pancreatic cancer, skin cancer, bladder cancer, or the like.

Diltiazem or an acid addition salt thereof can enhance the activity of various antitumor agents on tumor cells having resistance to the agents and is also effective for decreasing the dose of antitumor agents in both cases of resistant and non-resistant tumor cells, and hence, can alleviate the toxicity and side-effects of the antitumor agent administered to patients. Moreover, diltiazem of the present invention can enhance the antitumor activity of antitumor agents even on tumor cells having cross-resistance to the agents, and hence, the anti-tumor agent can be used without regard to the cross-resistance of tumor cells to the antitumor agents insofar as it is administered to patients together with diltiazem. The present invention is illustrated by the following Examples but should not be construded to be limited thereto.

EXAMPLE 1

Effects on P388 leukemia cells having resistance to vincristine:

A medium (2 ml) containing P388 leukemia cells ($3.0 \times 10^4$) having resistance to vincristine (hereinafter, referred to as "VCR") is incubated at 37° C. in a wet atmosphere containing 5% carbon dioxide gas in a cultivation tube. After cultivation for 24 hours, a solution of diltiazem hydrochloride and VCR in a physiological saline solution is added to the culture broth, and the mixture is further cultivated.

As a control, the above procedure is repeated except that VCR alone is added to the culture broth.

After cultivation for 48 hours, the number of cells in the culture broth is counted in a Coulter counter. The growth-inhibitory effect is measured by plotting the concentration of the agent and growth ratio (ratio of growth rate in agent-treated cells to that in control) on a graph and reading the concentration of the agent ($IC_{50}$) in which the growth of cells is inhibited by 50%. The results are shown in the accompanying figure, wherein each line means the growth rate of cells treated with (1) VCR alone, (2) combination of VCR and diltiazem (10 μM), (3) combination of VCR and diltiazem (35 μM), and (4) combination of VCR and diltiazem (100 μM).

EXAMPLE 2

Antitumor enhancement effects in mice inoculated with VCR-resistant P388 leukemia cells:

$CDF_1$ female mice weighing 20–23 g (one group: 5 mice) are intraperitoneally inoculated with a diluted ascites fluid containing VCR-resistant P388 leukemia cells ($1 \times 10^6$). Separately, two solutions of VCR and diltiazem hydrochloride in 0.9% aqueous saline solution are prepared and are mixed. The mixture is intraperitoneally administered to the mice in a dose of 0.01 ml/g of body weight for 10 days after inoculation of the leukemia cells.

The antitumor enhancement effects are evaluated by the ratios: T/C and T/V expressed by the following equations:

$$\frac{T}{C} = \frac{\text{Mean survival day of the treated group}}{\text{Mean survival day of the untreated group}} \times 100$$

$$\frac{T}{V} = \frac{\text{Mean survival day of the group treated with both antitumor agent and diltiazem}}{\text{Mean survival day of the group treated with VCR alone}} \times 100$$

The results are shown in Table 1.

TABLE 1

| Agent administered | | Antitumor enhancing effect | | |
|---|---|---|---|---|
| VCR (μg/kg) | Diltiazem HCl (mg/kg) | Survival time (day) | T/C (%) | T/V (%) |
| — | — | 11.4 ± 1.2 | 100 | — |
| — | 100 | 11.8 ± 0.4 | 104 | — |
| 30 | — | 10.6 ± 2.1 | 93 | 100 |
|  | 60 | 11.8 ± 1.9 | 104 | 111 |
|  | 80 | 13.8 ± 2.3 | 121 | 130 |
|  | 100 | 12.2 ± 1.3 | 107 | 115 |
|  | 125 | 13.6 ± 1.9 | 119 | 125 |
| 100 | — | 10.8 ± 1.3 | 95 | 100 |
|  | 60 | 13.8 ± 1.7 | 121 | 128 |
|  | 80 | 14.4 ± 1.5 | 126 | 133 |
|  | 100 | 15.0 ± 0.9 | 132 | 139 |
|  | 125 | 15.0 ± 1.5 | 132 | 139 |
| 200 | — | 12.4 ± 1.0 | 109 | 100 |
|  | 60 | 14.8 ± 1.2 | 130 | 119 |
|  | 80 | 14.8 ± 0.7 | 130 | 119 |
|  | 100 | 15.8 ± 0.7 | 139 | 127 |
|  | 125 | 17.0 ± 1.2 | 149 | 137 |

EXAMPLE 3

Antitumor enhancement effect in mice inoculated with ADM-resistant P388 leukemia cells:

$CDF_1$ female mice weighing 20-23 g (one group: 5 mice) are intraperitoneally inoculated with a diluted ascites fluid containing P388 leukemia cells ($1 \times 10^5$) having resistance to doxorubicin (hereinafter referred to as "ADM"). Separately, two solutions of ADM and diltiazem hydrochloride in 0.9% aqueous saline solution are prepared and are mixed. The mice are treated in the same manner as described in Example 2, and the antitumor enhancement effect of diltiazem to ADM is evaluated likewise.

The results are shown in Table 2.

TABLE 2

| Agent administered | | Antitumor enhancing effect | | |
|---|---|---|---|---|
| VCR (mg/kg) | Diltiazem HCl (mg/kg) | Survival time (day) | T/C (%) | T/V (%) |
| — | — | 12.6 ± 0.5 | 100 | — |
| — | 125 | 13.0 ± 0 | 103 | — |
| 0.5 | — | 13.6 ± 0.8 | 108 | 100 |
|  | 80 | 16.2 ± 2.4 | 129 | 119 |
|  | 100 | 15.2 ± 0.4 | 121 | 112 |
|  | 125 | 15.6 ± 0.8 | 124 | 115 |
| 1.0 | — | 14.8 ± 0.7 | 117 | 100 |
|  | 80 | 15.8 ± 0.4 | 125 | 107 |
|  | 100 | 16.0 ± 0.6 | 127 | 108 |
|  | 125 | 17.6 ± 1.7 | 140 | 119 |
| 1.5 | — | 14.6 ± 1.2 | 116 | 100 |
|  | 80 | 16.2 ± 1.2 | 129 | 111 |
|  | 100 | 16.2 ± 0.7 | 129 | 111 |
|  | 125 | 17.8 ± 1.8 | 141 | 121 |

EXAMPLE 4

Antitumor enhancement effects of diltiazem in resistant and non-resistant tumor cells:

In the same manner as described in Example 1 except that P388 leukemia cells having no resistance or resistance to VCR and ADM and human leukemia cells K562 are used as the tumor cells and VCR, ADM are used alone or with diltiazem hydrochloride as the agent, the concentration of agents for 50% growth-inhibition is measured likewise.

The results are shown in Table 3 (as to data of ADM) and Table 4 (as to data of VCR), respectively. As is shown in these tables, the antitumor activity of the agents is enhanced by diltiazem regardless of whether the tumor cells are non-resistant or resistant.

TABLE 3

| (Enhancement effects on ADM) | | | | |
|---|---|---|---|---|
|  | P388 | | P388/ADM | |
| Diltiazem (μM) | $IC_{50}$ (ng/ml) | Enhancement effect | $IC_{50}$ (ng/ml) | Enhancement effect |
| 0 | 10.0 ± 2.1 | 1 | 592 ± 76.8 | 1 |
| 10 | 7.7 ± 3.6 | 1.3 | 133 ± 18.4 | 4.5 |
| 35 | 6.9 ± 0.7 | 1.4 | 53.7 ± 3.1 | 11.0 |
| 100 | 6.0 ± 0.4 | 1.7 | 30.7 ± 4.1 | 19.3 |

TABLE 4

| (Enhancement effects on VCR) | | | | |
|---|---|---|---|---|
| Diltiazem (μM) | $IC_{50}$ (ng/ml) | Enhancement effect | $IC_{50}$ (ng/ml) | Enhancement effect |
|  | P388 | | P388/VCR | |
| 0 | 1.88 ± 0.13 | 1 | 29.7 ± 2.87 | 1 |
| 10 | 1.43 ± 0.12 | 1.3 | 3.07 ± 0.09 | 9.7 |
| 35 | 0.56 ± 0.06 | 3.4 | 1.03 ± 0.06 | 28.8 |
| 100 | 0.45 ± 0.02 | 4.2 | 0.55 ± 0.17 | 54.0 |
|  | K562 | | K562/VCR | |
| 0 | 2.33 ± 0.24 | 1 | 200 ± 16.3 | 1 |
| 10 | 1.52 ± 0.09 | 1.5 | 23 ± 2.16 | 8.7 |
| 35 | 1.00 ± 0.17 | 2.3 | 4.1 ± 0.36 | 48.8 |
| 100 | 0.69 ± 0.10 | 3.4 | 2.57 ± 0.41 | 77.8 |

EXAMPLE 5

Antitumor enhancement effect of diltiazem in solid tumor cells:

Antitumor enhancement effects of diltiazen to VCR are evaluated in $B_{16}$ melanoma tumor cell lines ($B_{16}$ mix, $F_{10}$, $F_1$, $B_2$ and BL-6), and colon 26 tumor cell lines ($C_{26}$ mix, NL-33, N-1, N-5, and KL-2).

The experiment is carried out in the same manner as described in Example 2, wherein the tumor cells are cultivated for 24 hours and after treated with the agents, the cultivation is done for 72 hours, and the $IC_{50}$ is measured likewise.

The results are shown in Table 5.

TABLE 5

| Diltiazem (μM) | $B_{16}$ melanoma cells* | | | | |
|---|---|---|---|---|---|
|  | $B_{16}$ mix | $F_{10}$ | $F_1$ | $B_2$ | BL-6 |
| 0 | 2.6 ± 0.87 (1.0) | 7.4 ± 0.6 (1.0) | 8.6 ± 3.8 (1.0) | 5.15 ± 0.64 (1.0) | 5.4 ± 0.2 (1.0) |
| 10 | 1.75 ± 0 (1.5) | 3.0 ± 0.61 (2.5) | 2.07 ± 0.29 (4.2) | 3.37 ± 0.76 (1.5) | 2.22 ± 0.35 (2.5) |
| 100 | 1.21 ± 0.51 (2.1) | 1.63 ± 0.12 (4.5) | 0.67 ± 0.11 (12.8) | 1.62 ± 0.28 (3.2) | 1.68 ± 0.18 (3.2) |
|  | Colon 26 tumor cells* | | | | |
|  | $C_{26}$ mix | NL-33 | N-1 | N-5 | KL-2 |
| 0 | 17.8 ± 2.6 (1.0) | 35.8 ± 2.6 (1.0) | 25.4 ± 2.3 (1.0) | 15.8 ± 0.3 (1.0) | 11.0 ± 0.3 (1.0) |

TABLE 5-continued

| Diltiazem ($\mu$M) | | | | | |
|---|---|---|---|---|---|
| 10 | 2.65 ± 0.50 (6.7) | 16.1 ± 6.3 (2.2) | 4.96 ± 0.56 (5.1) | 5.78 ± 0.45 (2.7) | 2.47 ± 0.02 (4.5) |
| 35 | 1.56 ± 0.19 (11.4) | 5.77 ± 0.33 (6.2) | 2.04 ± 0.25 (12.5) | 2.03 ± 0.35 (7.8) | 1.72 ± 0.04 (6.4) |

*Number in the table is IC$_{50}$ dose (mg/ml) of VCR, and the number within parenthesis is ratio of IC$_{50}$ dose in the group treated with both of VCR and diltiazem to that of the group treated with VCR alone (which means the enhancement effect of diltiazem).

Clinical Test 1

The patient was a man (36 years old) who had subjective symptoms of lymphadenoma at left armpit and was diagnosed as Hodgkin's disease (nodular sclerosis) by biopsy and then entered a hospital. He was subjected to MOPP therapy (cf. Ann. intern. Med., 73, 881–895, 1970) as Clinical Stage IIIa (cf. Cancer Research, Vol. 31 (1971), 1860–1861). That is, on the first day, vincristine sulfate (1.4 mg/m$^2$) and nitrogen mustard (6 mg/m$^2$) were intravenously injected and further procarbazine hydrochloride (100 mg/m$^2$) and prednisone (40 mg/m$^2$) were orally administered to the patient, said procarbazine hydrochloride and prednisone being everyday administered and being continued for 14 days, and said vincristine sulfate and nitrogen mustard being administered on the first day and 8th day in the same dose. From 14th day to 28th day no drug was administered. Above treatment cycle was repeated for about 6 months (totally 6 cycles), but no reduction of the lymphadenoma was observed. About one month after the above MOPP therapy, diltiazem hydrochloride (90 mg) was administered to the patient in addition to the MOPP therapy.

As a result, the lymphadenoma was temporarily remarkably reduced. Although the lymphadenoma was again enlarged after about one month, it was reduced by administering diltiazem (180 mg per day, which was divided and administered in three times per day) for 4 days.

During the treatment no side effect was observed.

Clinical Test 2

The patient was a woman (36 years old) who firstly showed increase of leukocytes (9200/$\mu$l) at 6 weeks of pregnancy and was diagnosed as a chronic myeloplast by detailed inspection. She was firstly administered with Busulfan (1,4-butanediol dimethanesulfonate) for about one year. Thereafter, she showed symptoms of right genicularathralgia, pyrexia, increase of splenoma and increase of leukocytes, which were doubtful of Blastic crisis, and hence, she entered a hospital. In the hospital, she was administered with vincristine (1 mg per week) and predonisolone (60 mg per day). As a result, the number of leukocytes and the splenoma were temporarity somewhat recovered, but even after third administration of viscristine (1 mg per week), the number of leukocytes and the splenoma still increased, and hence, diltiazem hydrochloride was administered in a dose of 180 mg per day, which were divided and administered in three times per day, for 4 days in addition to the administration of vincristine (1 mg/week). As a result, both symptoms were remarkably improved and the effect was continued for about two weeks.

During the treatment no side effect was observed.

What is claimed is:

1. A pharmaceutical composition useful for treating or preventing a tumor selected from the group consisting of chronic lymphatic leukemia, chronic myelogenous leukemia and Hodgkin's disease which comprises 10 mg to 120 mg of diltiazem or a pharmaceutically acceptable acid addition salt thereof and 3 $\mu$g to 30 mg of a compound selected from the group consisting of vincristine and doxorubicine.

2. The composition according to claim 1, wherein said compound is vincristine.

3. The composition according to claim 1, wherein said compound is doxorubicine.

* * * * *